United States Patent
Ayyapanpillai et al.

(10) Patent No.: US 8,372,649 B2
(45) Date of Patent: Feb. 12, 2013

(54) END-CAPPED BIPYRIDINE COMPOUND, PROCESS FOR PREPARATION THEREOF AND PROCESS FOR SELECTIVE DETECTION OF CYANIDE ANIONS THEREWITH

(75) Inventors: Ajayaghosh Ayyapanpillai, Kerala (IN); Sreejith Sivaramapanicker, Kerala (IN); Divya P Kizhumuri, Kerala (IN); Jayamurthy Purushothaman, Kerala (IN)

(73) Assignee: Council of Scientific & Industrial Research (IN)

( * ) Notice: Subject to any disclaimer, the term of this patent is extended or adjusted under 35 U.S.C. 154(b) by 0 days.

(21) Appl. No.: 13/421,511

(22) Filed: Mar. 15, 2012

(65) Prior Publication Data

US 2012/0231547 A1    Sep. 13, 2012

Related U.S. Application Data

(63) Continuation of application No. PCT/IN2010/000623, filed on Sep. 15, 2010.

(30) Foreign Application Priority Data

Sep. 15, 2009  (IN) ............................ 1899/DEL/2009

(51) Int. Cl.
*G01N 33/48* (2006.01)
*G01N 21/64* (2006.01)
*C07D 213/22* (2006.01)

(52) U.S. Cl. .................. 436/109; 422/82.05; 422/82.08; 422/82.09; 422/420; 422/424; 422/425; 422/429; 422/430; 436/106; 436/164; 436/166; 436/169; 436/172; 546/10; 546/255; 546/256; 546/257; 546/268.1; 546/276.4; 546/276.7; 546/279.7; 546/280.4

(58) Field of Classification Search ............... 422/82.05, 422/82.08–82.09, 420, 424–425, 429–430; 436/106, 109, 164, 166, 169, 172; 546/10, 546/255–257, 268.1, 276.4, 276.7, 279.7, 546/280.4
See application file for complete search history.

(56) References Cited

FOREIGN PATENT DOCUMENTS

WO    2009084007 A1    7/2009

OTHER PUBLICATIONS

Wang, B. et al, Journal of the American Chemical Society 1997, 119, 12-21.*
Guidelines for Drinking-Water Quality—Second Edition—vol. 2—Health Criteria and Other Supporting Information; (c) World Health Organization: Geneva, 1996; pp. 1-94.
Ullman's Encyclopedia of Industrial Chemistry; Toxicology, 1. Fundamentals; Wiley-VCH: New York, 1999; pp. 127-211.
R. Koenig, "Wildlife Deaths Are a Grim Wake-Up Call in Easter Europe"; Science, Mar. 10, 2000, 287, pp. 1737-1738 (3 page pdf).
Ajayaghosh, et al.; "A Radiometric Fluorescence Probe for Selective Visual Sensing of Zn" Journal of American Chemical Society 2005, vol. 127; pp. 14962-14963.

* cited by examiner

*Primary Examiner* — Arlen Soderquist
(74) *Attorney, Agent, or Firm* — St. Onge Steward Johnston & Reens LLC

(57) ABSTRACT

The present invention describes the development of a end-capped bipyridine compound having formula A and the zinc complex having formula B. The assay having formula 1 can be used to estimate and quantify the amount of zinc ions by monitoring the fluorescence changes. The assay with formula 1 can be use to image and detect $Zn^{2+}$ ions in MCF7 cell lines. The zinc complex of formula 2 and 4 can be used as a fluorescent sensor for cyanide anions using analyte replacement protocol. The assay with formula 2 is selective only to cyanide anions even in the presence of other competing anions. The assay with formula 3 having bright green solid state emission is used for the preparation of formula 4. The orange fluorescent powder of assay with formula 4 is used for the selective detection of CN⁻ ions in aqueous solution.
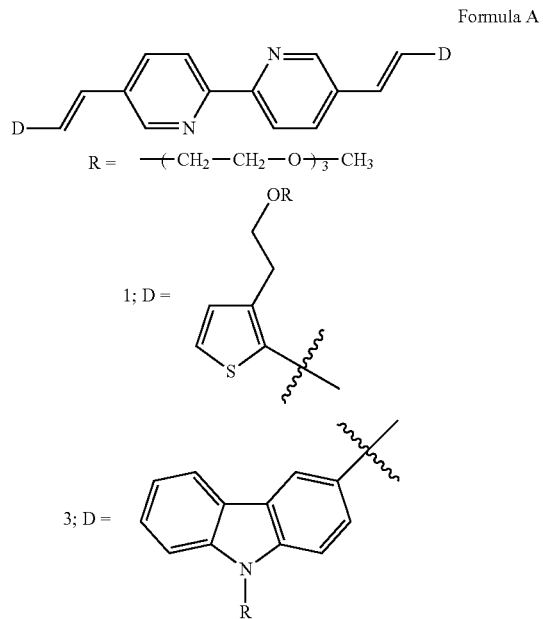
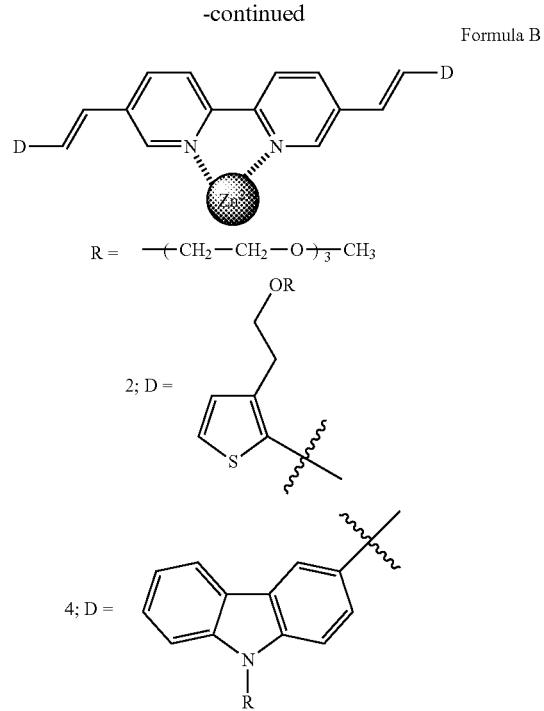
7 Claims, 6 Drawing Sheets

Figure 1:
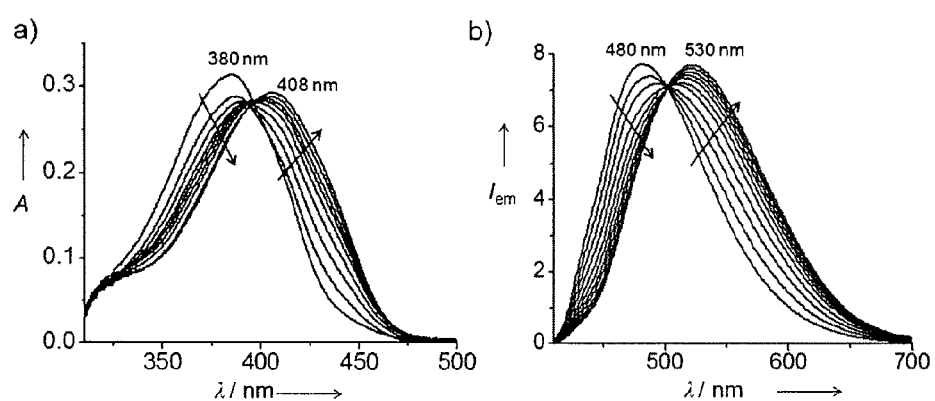

END-CAPPED BIPYRIDINE COMPOUND, PROCESS FOR PREPARATION THEREOF AND PROCESS FOR SELECTIVE DETECTION OF CYANIDE ANIONS THEREWITH

CROSS-REFERENCE TO RELATED APPLICATIONS

The present application is a continuation of pending International patent application PCT/IN2010/000623 filed on Sep. 15, 2010 which designates the United States and claims priority from Indian patent application 1899/DEL/2009 filed on Sep. 15, 2009.

FIELD OF INVENTION

The present invention relates to an end-capped bipyridine of general formula A and its zinc complex. The present invention particularly relates to thiophene end-capped bipyridine assay having the formula 1 for selective detection of cyanide anions and the process thereof. The thiophene end-capped bipyridine assay (formula 1) complexes with zinc ions in aqueous conditions resulting in a fluorescent complex (formula 2). The assay-zinc complex formula 2 can be used for cyanide anion detection using an analyte replacement protocol to a level in the range of 0.10 ppm. The assay having formula 2 is selective to cyanide anions among other competing cations. Among all the other cations the assay having formula 1 form fluorescent complex only with zinc ions. The assay with formula 1 can also be used to image $Zn^{2+}$ in MCF7 cell lines. The appropriate modification of formula 1 (replacement of thiophene with carbazole) gives formula 3. The assay powder (formula 4) prepared by the complexation of zinc with formula 3 show high solid state fluorescence which is useful for device fabrication. The prepared device in particular can be used for selective detection of cyanide ions ($CN^-$) from aqueous solutions containing different anions.

The present assaying for cyanide anion is simpler and, does not require sophisticated instruments. The fluorescence property of the assay having formula 2 is significantly changed when it is in contact with cyanide anions. The application of the assay is demonstrated by analyzing the presence of cyanide anion content in cyanogenic glycosides presents in Cassava plant (*Manihot esculenta*), which is a potential cyanide food poisoning when taken in raw.

Formula 1

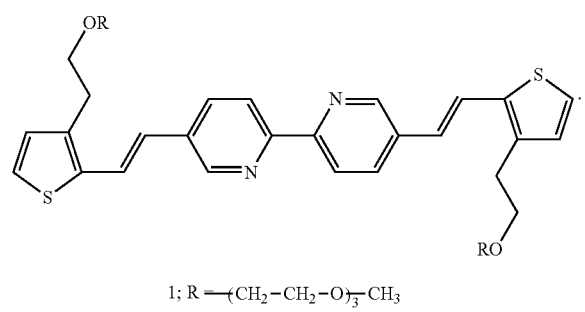

1; R = —(CH$_2$—CH$_2$—O)$_{\overline{3}}$—CH$_3$

Formula 2

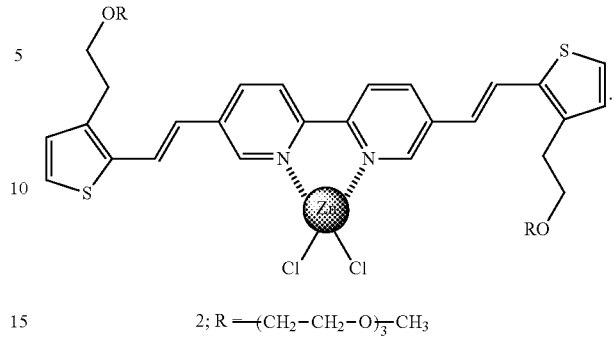

2; R = —(CH$_2$—CH$_2$—O)$_{\overline{3}}$—CH$_3$

Formula 3

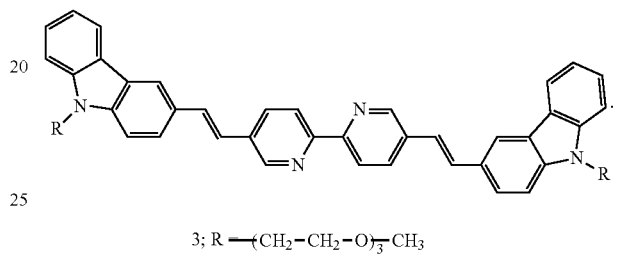

3; R = —(CH$_2$—CH$_2$—O)$_{\overline{3}}$—CH$_3$

Formula 4

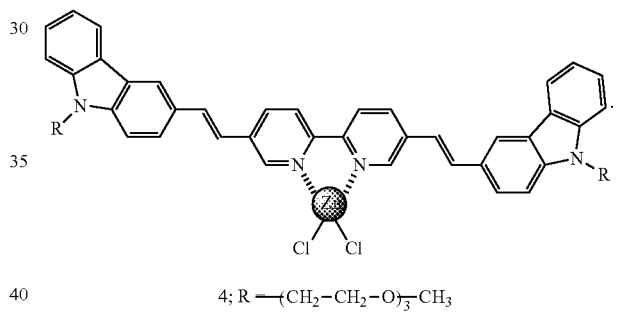

4; R = —(CH$_2$—CH$_2$—O)$_{\overline{3}}$—CH$_3$

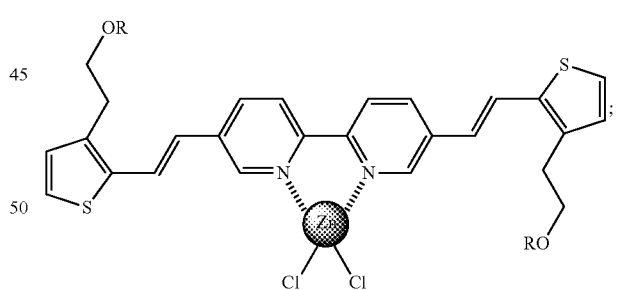

R = —(CH$_2$—CH$_2$—O)$_{\overline{3}}$—CH$_3$

BACKGROUND OF THE INVENTION

Detection and estimation of anions have received considerable attention for their important roles in biological, industrial, and environmental processes. In particular, cyanide is a highly toxic anion for living system. However, cyanide is widely used for industrial applications, which releases cyanide into the environment as a toxic contaminant. The World Health Organization (WHO) has set the maximum contaminant level (MCL) of cyanide in drinking water to be 1.9 μM (0.04 ppm) and a greater content can have acute effects. This is of paramount importance particularly after the accidental cyanide spill in Romania in the year 2000 which is considered to be one of the worst disasters in Europe since Chernobyl. The detection of $CN^-$ is also important since many plants and fruits are known to contain cyanides. Most of the reported probes are colorimetric or fluorescence dosimeters (indicators), useful for the one time detection of the analyte. References may be made to: a) *Guidelines for Drinking-Water Quality*, World Health Organization: Geneva, 1996; b) *Ullman's Encyclopedia of Industrial Chemistry*, Wiley-VCH: New York, 1999; c) G. C. Miller, C. A. Pritsos, *Cyanide: Social Industrial and Economic Aspects; Proceedings of the TMS Annual Meeting*, 2001 pp 73-81; d) R. Koenig, Science, 2000, 287, 1737; e) A. W. Hayes, *Principles and Methods of Toxicology*, 5th ed. Taylor and Francis, Boca Raton, Fla.

The main disadvantages which have prevented the practical application of molecular probes for the detection of metals ions especially, potentially dangerous anions such as cyanide, in aqueous media at normal conditions are;
1) that the detection requires professional laboratory type operations, such as precise transfer of solutions, usage of sophisticated instrumental techniques etc., making it less useful to people who do not have any scientific background.
2) the low sensitivity and selectivity of the probes towards cyanide anions for an instrument free observation. For example, a probe which can distinguish analyte binding by color change or fluorescence change with naked eye.
3) compatibility of the probe in aqueous conditions and at the same time it should interact with cyanide anions in solution. An ideal fluorophore must have comparatively good quantum yield under aqueous conditions.
4) The fourth and significant one is the difficulty in reprocessing and thereby multiple use of the probe.

OBJECTS OF THE INVENTION

The main object of the present invention is to provide a end-capped bipyridine having the formula A and its zinc complex of formula B for selective detection of cyanide anions and the process thereof.

Another object of the present invention is to develop a flawless technique for detecting cyanide anions using a relatively simple and convenient technique, specifically necessary for the practical application of molecular probes as sensors for potentially dangerous anions such as cyanide ($CN^-$).

Yet another objective of the present invention is to provide an accurate, fast, real time method for the assay of cyanide anions in aqueous samples.

Another main objective of the present invention is to develop a new fluorescent $Zn^{2+}$ specific probe for detecting $Zn^{2+}$ in cellular environments. The present invention aims to use $Zn^{2+}$ specific fluorophore with formula 1 for imaging and detecting $Zn^{2+}$ ions in cellular environments. Presence of $Zn^{2+}$ ions in live MCF7 cell lines were detected using assay with formula 1. Similar to the detection of zinc ions form aqueous analytical solutions using solid state fluorescence changes (Reference may be made to: PCT/IN2008/000374), using the current methodology zinc ions can be detected using assay having formula 1 from cultured cell lines. The water solubility, cell permeability as well as the less toxicity of probe with formula 1 is advantageous in cell imaging over the file patent.

BRIEF DESCRIPTION ABOUT THE DRAWINGS

These and other features, aspects, and advantages of the present invention will become better understood with reference to the following description and appended claims and accompanying drawings where:

Formula 1 represents formula of thiophene bipyridine assay 1 which is a selective fluorescent probe for zinc ions.

Formula 2 represents formula of zinc complex of thiophene bipyridine assay 1 ie, assay 2 which is can be used as a selective fluorescent probe for cyanide anions using zinc ion displacement strategy.

Formula 3 represents formula of carbazole bipyridine assay 3 which is a selective fluorescent probe for zinc ions.

Formula 4 represents formula of zinc complex of carbazole bipyridine assay 3 ie, assay 4 is used for the fabrication of device for the detection of $CN^-$ ions in aqueous solution.

FIG. 1 shows the changes in the a) absorption and b) emission ($\lambda_{ex}$=390 nm) spectra of probe (Formula 1) in acetonitrile/water (4:1 HEPES buffer, 0.01M) at pH 7.2 with the addition of one equivalent zinc ions.

Figure 2:
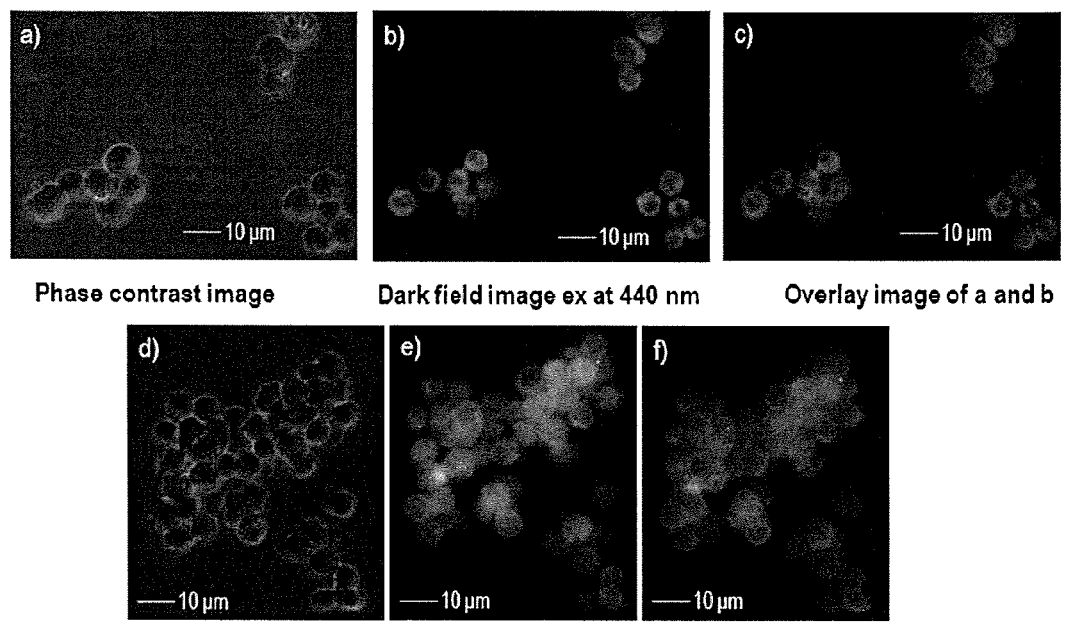

FIG. 2 shows fluorescence image of MCF7 cell lines. a) phase contrast image of cell lines with assay having formula 1. b) dark field image showing fluorescence of assay 1. c) overlay image of a and b. d) phase contrast image of cell lines incubated with $Zn^{2+}$. e) fluorescence dark field image of green fluorescence corresponding to assay 1. $Zn^{2+}$ complex. f) overlay image of a and e.

Figure 3:
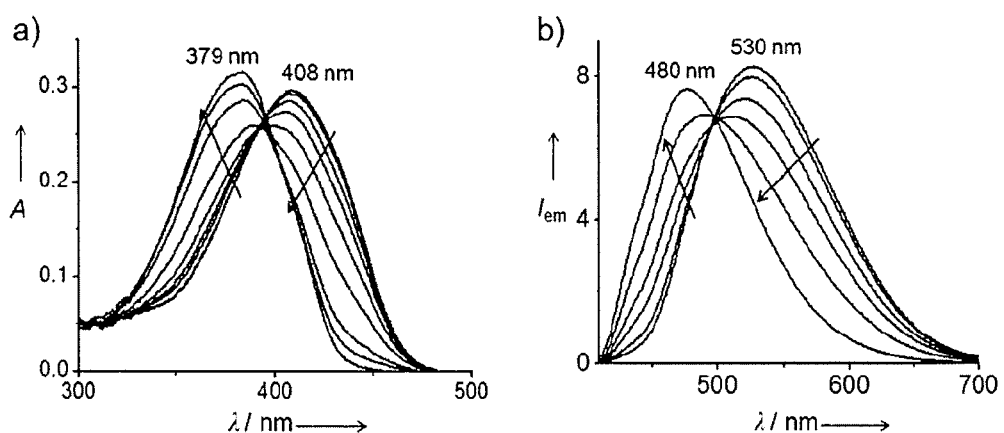

FIG. 3 shows the changes in the a) absorption and b) emission ($\lambda_{ex}$=390 nm) spectra of assay 2 (Formula 2) in acetonitrile/water (4:1 HEPES buffer, 0.01M) at pH 7.2 with the addition of tetrabutyl ammonium cyanide (four equivalents).

Figure 4:
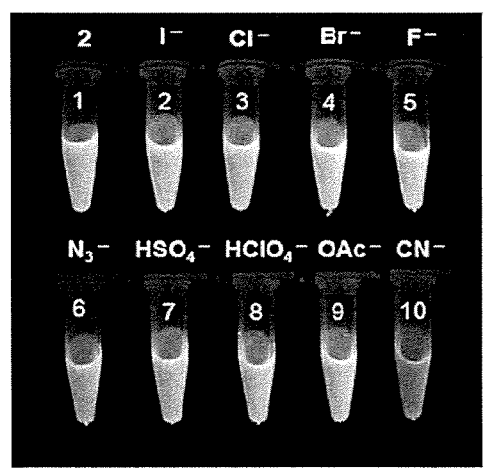

FIG. 4 shows the photograph showing selective visual detection of cyanide anions using assay 2. Sample vials contain assay 2 alone [$6\times10^{-6}$ M] (vial 1), and 20 time excess of tetra butyl ammonium salts of different anions (vials 2-10). Example 6.

Figure 5:
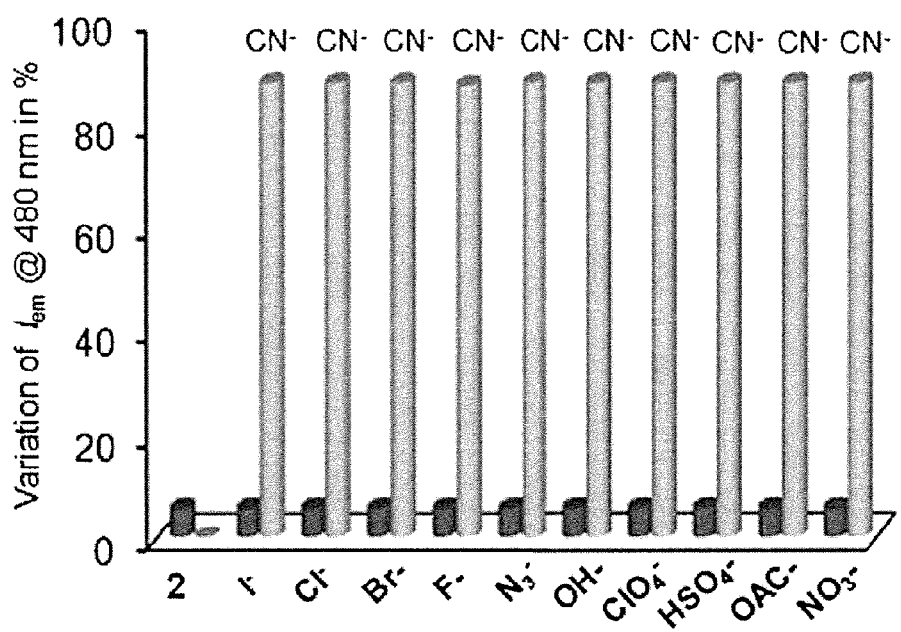

FIG. 5 shows the plot showing the response of assay 2 [$6\times10^{-6}$ M] to different anions. The emission intensity is monitored at 480 nm in acetonitrile-water (4:1) (HEPES buffer 0.01M, pH 7.2). Black bars represent response of assay 2 with different anions. Gray bars shows the enhancement in emission of assay 2 with $CN^-$ in the presence of excess of (20 times) of different anions. All emission intensities were recorded in Bio-Tek Cell reader using 96-well plate, 200 µL per well.

Figure 6:
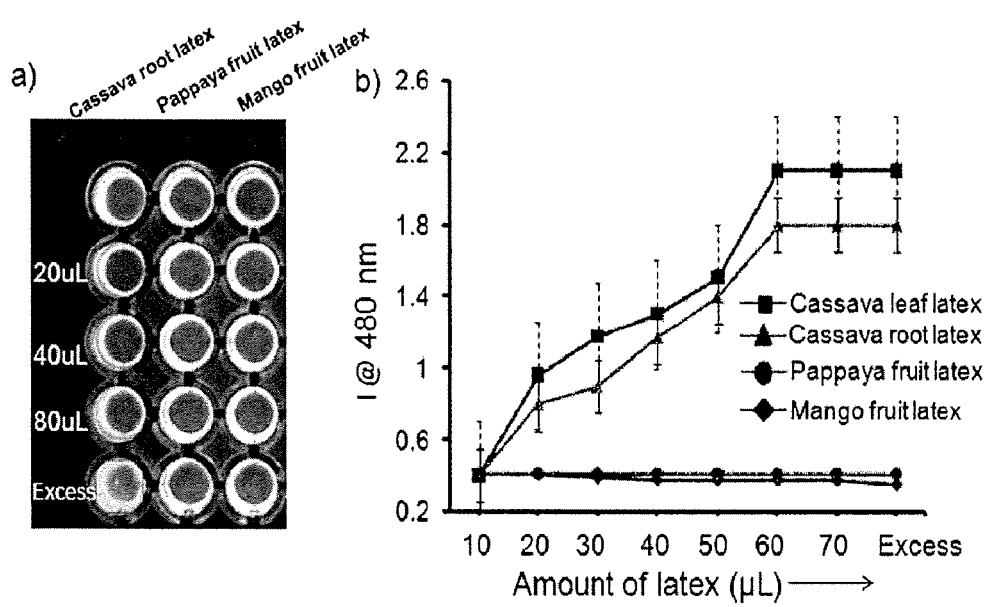

FIG. 6 represents a) 96 well plate showing the emission changes of assay 2 with the addition of (0, 20, 40, 80 µL and in excess) cassava leaf latex (first column wells), papaya latex (second column wells) and unripe mango fruit latex (third column wells), illuminated using 365 nm UV light, b) Plot showing the increase in the emission intensity of assay 2 ($6\times10^{-6}$ M) at 480 nm ($\bullet_{ex}$ @ 315 nm) upon addition of different aliquots of different leaf, tuber juices from cassava, and fruit juices from papaya and mango. The red and green graph shows the changes with leaf (error limit ±0.3) and tuber latex (error limit ±0.15) from MNga1 variety of edible cassava plant.

Figure 7:
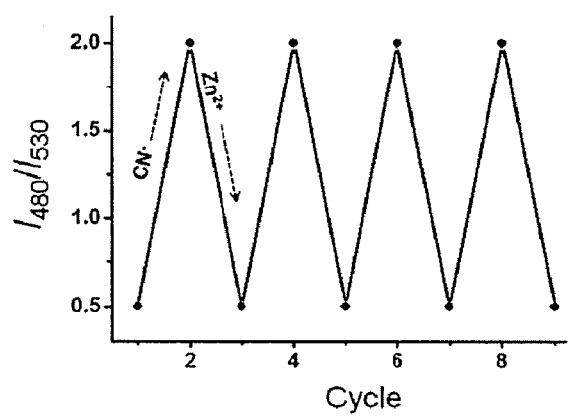

FIG. 7 represents Ratiometric fluorescence responses of assay 4 during eight continuous cycles of addition of $CN^-$ and $ZnCl_2$.

Figure 8:
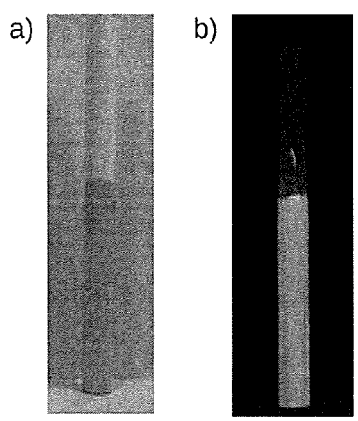

FIG. 8 Photograph of the performance of the device with $CN^-$ ions in aqueous medium a) photograph of the device in visible light, b) photograph of the device illuminated by 365 nm light.

Figure 9:
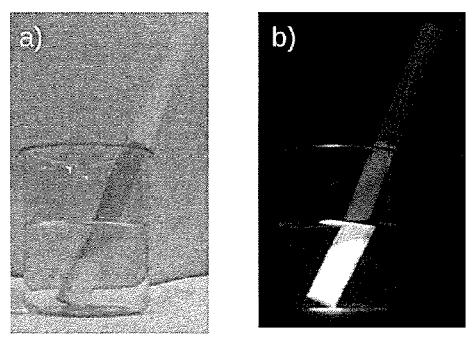

FIG. 9 Photograph of the dipstick device showing its performance in aqueous solution of tetrabutyl ammonium cyanide ($2\times10^{-4}$ M); a) dipstick prepared using thermoplastic under visible light, b) illuminated under 365 nm UV light.

SUMMARY OF THE INVENTION

Accordingly the present invention provides an end-capped bipyridine of general formula A and its zinc complex

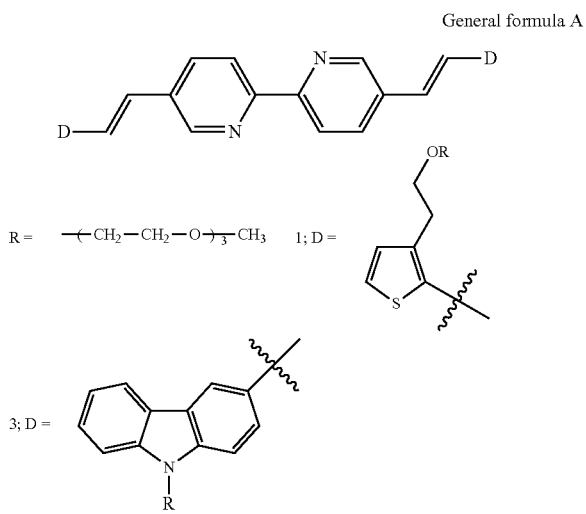

wherein the zinc complex comprising the general formula B

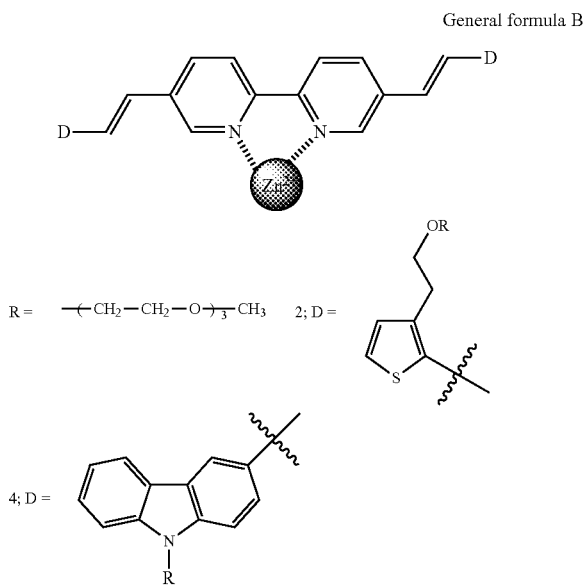

In an embodiment of the invention wherein the Zinc complex of formula 2 and 4 are useful for the detection and estimation of cyanide anions in aqueous analytical and biorelevant samples.

Accordingly the present invention provides a process for preparation of end-capped bipyridine compound of formula A and its zinc ion complex of formula B as claimed in claims 1 and 2 wherein the process steps comprising;

(i) reacting 5,5'-dimethyl-2,2'-bipyridine and N-bromosuccinimide in dry carbon tetrachloride in presence of azobisisobutyronitrile (AIBN) as catalyst in the ratio of 10 mmol:20.5 mmol, in carbon tetrachloride at temperature ranging between 80-85° C., for a period ranging between 18-20 h, (ii) cooling the reaction mixture and filtering to obtain the filterate, removing the solvent under reduced pressure to obtain the compound 5,5'-bis(bromomethyl)-2,2'-bipyridine (bisbromomethyl), (iii) reacting 5,5'-bis(bromomethyl)-2,2'-bipyridine (bisbromomethyl) obtained in step (ii) with triethylphosphite as reactant cum solvent in the ratio of 2 mmol:3 ml, at a temperature ranging between 80-85° C., for about 10-12 h, at normal pressure, and purifying by partial vacuum to obtain 5,5'-Bis-(diethyl phosphonomethyl)-2,2'-bipyridine (Bisphosphonate), (iv) reacting 5,5'-Bis-(diethyl phosphonomethyl)-2,2'-bipyridine (Bisphosphonate) (2 mmol) with 3-(2,5,8,11-tetraoxamidecan-13-yl)thiophene-2-carbaldehyde (glycolated thiophene carbaldehyde) or glycolated carbazole carbaldehyde (4 mmol) in presence of sodium hydride (12 mmol); in 30 ml THF at a refluxing temperature of 65-70° C., for a period ranging between 10-15 h, to obtain the compound of general formula A (compound 1 and 3 respectively), (v) reacting the compound of general formula A with $ZnCl_2$ to obtain the zinc complex of formula B.

In another embodiment of the invention wherein the glycolated thiophene carbaldehyde or glycolated carbazole carbaldehyde is prepared reacting 3-(2,5,8,11-tetraoxamidecan-13-yl)thiophene or glycolated carbazole with phosphorus oxychloride in presence of DMF for a period ranging 12 hr at 27° C.

In another embodiment of the invention wherein the compounds are useful for the analysis of CN ions wherein the method of processing for quantitative analysis of $CN^-$ anions using the compound of formula 2 comprises:

(i) adding assay of formula 2 in acetonitrile/water mixture having acetonitrile and water in the ratio of 4:1 to the biological or clinical or industrial samples, (ii) determining the concentration of cyanide anions using UV absorption spectrometry and spectrofluorimetry.

In another feature of the invention wherein the compound of formula 1 is useful for an assay for imaging $Zn^{2+}$ ions in cellular environments, MCF7 cell lines were incubated $Zn^{2+}$ ions and the presence is detected and imaged with the help of fluorescence microscopy.

In yet another embodiment, the present invention provides a dipstick device useful for the selective detection of cyanide ions ($CN^-$) in solution comprising;

i) zinc complex of carbazole end capped bipyridine assay powder of formula 4 having bright orange fluorescence, adsorbed over alumina;

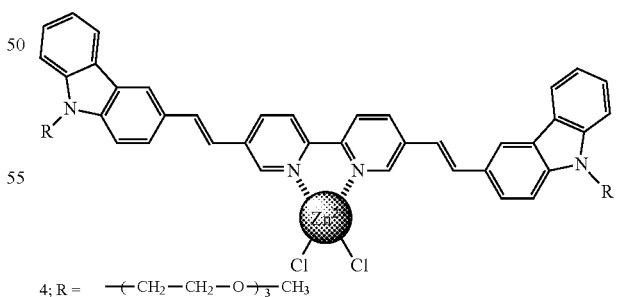

ii) the said material of step (i) being deposited or fixed over the surface of a thermoplastic strip support.

In another embodiment, the present invention provides a method for selective detection of cyanide anions ($CN^-$) in solution, using a dipstick device, wherein the step of detection comprises contacting the dipstick with a test sample, followed by monitoring a change in fluorescence colour, wherein a change in orange fluorescence colour to yellowish green colour indicates the presence of cyanide anions in the test sample.

In an embodiment of the invention wherein the device is useful for analytical sample containing lowest cyanide ions concentration $2\times10^{-4}$ M.

DETAILED DESCRIPTION OF THE INVENTION

To evaluate the amount of cyanide anions in biological samples and analytical samples, the present invention comprises of:
1) a thiophene end-capped bipyridine assay having general formula 1.
2) binding of the zinc ions into the assay (formula 1), resulted in green fluorescent cyanide probe, formula 2.
3) A carbazole end-capped bipyridine assay having formula 3.
4) Binding of zinc ions into formula 3, resulted in orange fluorescent cyanide probe, formula 4.
5) assay with formula 1 is used as a fluorescent probe for imaging and detecting $Zn^{2+}$ ions in MCF7 cell lines.
6) a zinc ion complex of assay 1 (formula 2), for the detection of potentially dangerous cyanide anions from aqueous and analytical solutions.
7) Assay with formula 4 is used for the fabrication of device
8) Method of displacement of zinc ions from assay with formula 2 as zinc cyanide complexes, lead to the regeneration of assay 1. The displacement event and thereby detection of cyanide anions can be signaled by color change as well as strong fluorescence change from green to blue using a 365 nm UV light.
9) Detecting the said signal from assay with formula 2 wherein said signal is proportional to the presence as well as the amount of cyanide anions.
10) Reusable nature of the said assay makes it more convenient and user friendly. Schematic representation of the synthesis of compounds specified in Example 1a and 1b, Example 2, Example 3 and Example 3 are shown below:

a. Scheme for the synthesis of 5,5'-bis(bromomethyl)-2,2'-bipyridine (bisbromomethyl), 4 (Example 1a)

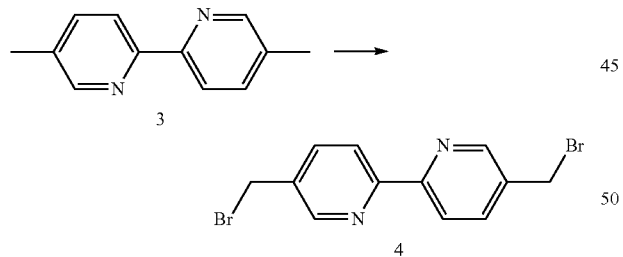

Reagents and conditions: NBS (N-bromosuccinimide), CCl₄ (carbon tetrachloride), AIBN (azobis isobutyronitrile), 18 h.

b. Scheme for the synthesis of 5,5'-Bis-(diethyl phosphonomethyl)-2,2'-bipyridine (Bisphosphonate), 5 (Example 1b)

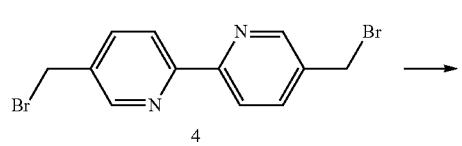

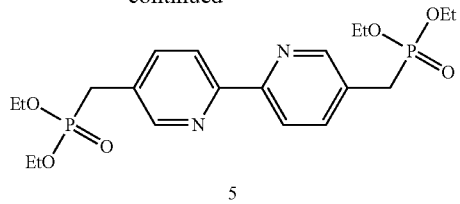

Reagents and conditions: P(OEt)₃ (Triethyl phosphite), 100•C, 12 h.

c. Scheme for the synthesis of 3-(2,5,8,11-tetraoxamidecan-13-yl)thiophene-2-carbaldehyde (glycolated thiophene carbaldehyde), 7 (Example 2a)

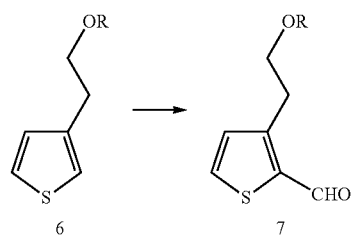

Reagents and conditions: POCl₃ (phosphorous oxychloride), DMF (dimethyl formamide), R=(—CH₂—CH₂—O—)₃—CH₃ d. Scheme for the synthesis of 1

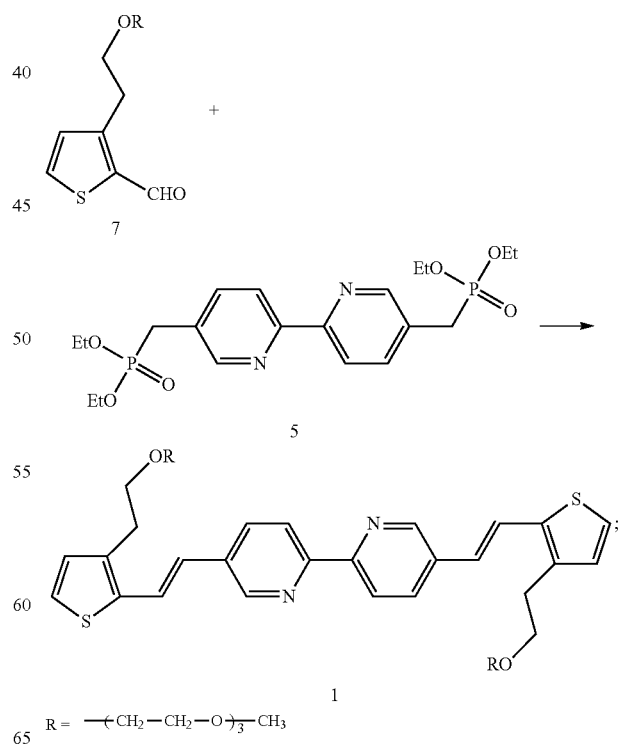

R = —(CH₂—CH₂—O)₃—CH₃

Reagents and conditions: NaH, THF, 70•C, 10 h.

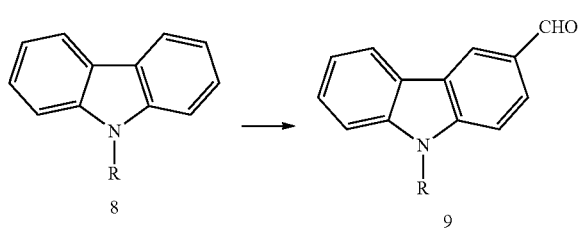

Reagents and conditions: POCl₃ (phosphorous oxychloride), DMF (dimethyl formamide), R =(—CH₂—CH₂—O—)₃—CH₃

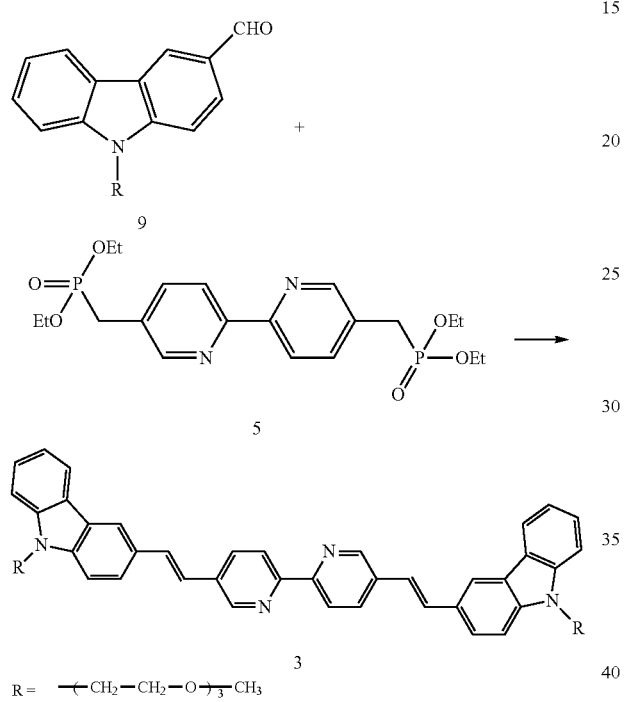

Reagents and conditions: NaH, THF, 65 deg C., 12 h.

The following MATERIALS and METHODS were used in the examples that follow.

The assay with formula 1, when complexes with $Zn^{2+}$ ions exhibits fluorescence change from blue to green. The fluorescence change is selective only for $Zn^{2+}$ ions. The cell permeable property of assay with formula 1 is used for imaging and detecting the presence of $Zn^{2+}$ ions in cellular environments. The presence of $Zn^{2+}$ ions in MCF7 cell lines were imaged with probe 1, using fluorescence microscope.

The assay having formula 2 when reacts with $CN^-$ anions results in the displacement of zinc ions and thereby generates the original fluorescence of the assay with formula 1. The assay with formula 2 can be prepared easily mixing a 1:1 proportion of formula 1 and $ZnCl_2$ solution in acetonitrile. The complexation can be followed by noting the color change from colorless to deep yellow and fluorescence change from deep green to deep blue. Thus by measuring the intensity of the emission formed or by comparing the ratio of emission intensity developed, the exact amount of cyanide anions in solutions can be estimated accurately. After the detection the probe having formula 2 can again be regenerated by adding excess amount of $ZnCl_2$ solution. Measuring the fluorescence using a fluorescence spectrophotometer allows the detection of cyanide anions up to 0.10 ppm. Fluorescence as well as the color changes in the solution can be recorded as visually graded photographs and can keep permanently as a record.

The probe has particular application to cyanide contaminated analytical samples and the detection event can be conducted at the location where the sample is found and this does not require any sophisticated technical support except using a portable 365 nm UV light source. The solution containing cyanide ions will result in the color change of the probe solution having formula 2 from yellow to color less. The probe provides rather important information by the change in fluorescence, which goes together with the color change. For cyanide anions the fluorescence of the solution of probe (formula 2) gets changed from bright green to deep blue. Monitoring the ratio of fluorescence intensity at two wavelengths (blue and green) provides significant information regarding concentration of cyanide anions in an analytical solution. Since the detection is based on the formation of zinc cyanide complexes other anions have no interference in the detection events. An intense blue fluorescence indicates high level of cyanide anions. Other competing anions such as $I^-$, $Cl^-$, $Br^-$, $HSO_4^-$, $OAc^-$, $HClO_4^-$, $N_3^-$ will not result in the changes in emission intensity in the green region.

The assay with formula 3, when a complex with zinc ions shows orange fluorescence. The fluorescence change is selective for zinc ions. The assay having formula 4 shows high solid state emission. The assay powder of formula 4 when coated over a thermoplastic can be used as a device for detection of cyanide in aqueous solution.

The following examples are given by way of illustration of the working of the invention in actual practice and should not be construed to limit the scope of the present invention in any way.

Example-1 a) Preparation of 5,5'-bis(bromomethyl)-2,2'-bipyridine (bisbromomethyl)

To a solution of 5,5'-dimethyl-2,2'-bipyridine (10 mmol) in 50 mL of dry carbontetrachloride was added N-bromosuccinimide (20.5 mmol) and AIBN. The reaction mixture was refluxed for 18 h, cooled, filtered and the solvents were removed under reduced pressure to give the crude product which was further purified by recrystallization from $CCl_4$. 88%; mp. 188° C.; $^1$H NMR ($CDCl_3$, 300 M Hz)•4.53 (s, 4H, $CH_2Br$), 7.79 (m, 2H, aromatic), 8.34 (m, 2H, aromatic), 8.61 (m, 2H, aromatic). $^{13}$C NMR ($CDCl_3$, 75 MHz)•29.43, 121.25, 133.28, 137.70, 149.27, 155.19.

b) Preparation of the 5,5'-Bis-(diethyl phosphonomethyl)-2,2'-bipyridine (Bisphosphonate)

Bisphosphonate were prepared by the reaction of the corresponding bisbromomethyl derivatives (2 mmol) with 3 mL of triethyl phosphite at 85° C. for 12 h followed by the removal of the unreacted triethyl phosphite by vacuum. Yield 90-95%; $^1$H NMR ($CDCl_3$, 300 MHz)•1.12 (m, 12H, $CH_3$), 3.21 (s, 4H, $CH_2P$), 4.14 (m, 8H, $OCH_2$), 7.34 (m, 2H, aromatic), 8.01 (m, 2H, aromatic), 8.30 (m, 2H, aromatic).

Example-2

(a) Preparation of 3-(2,5,8,11-tetraoxamidecan-13-yl)thiophene-2-carbaldehyde (glycolated thiophene carbaldehyde)

To a two-neck RB flask under argon atmosphere, $POCl_3$ (0.320 mL, 3.65 mmole) were taken and allowed to stir in an ice cold condition. Dimethyl formamide (DMF), (1.1 mL, 14.6 mmol) were added slowly into it. The reaction mixture was allowed to stir for 1 h. After the formation of the ylide (pale yellow color), glycolated thiophene (1 gm, 3.65 mmol) was added slowly into the reaction mixture. After 12 h, the reaction mixture was poured into ice water in a beaker. A fresh solution of 0.5 N NaOH was added and heated up to 80° C. The solution was then extracted with dichloromethane and purified using silica gel column chromatography (100-200 mesh, 30% ethylacetate-hexane as eluent). A pale yellow liquid was obtained. Yield 45%. $^1$H NMR (300 MHz, CDCl$_3$, TMS)•(ppm): 10.01 (s, —CHO), 7.05 (d, 1H, aromatic), 7.60 (d, 1H, aromatic), 3.6 (t, 2H), 3.5 (m, 12H), 3.38 (s, —OCH$_3$); $^{13}$C NMR CDCl$_3$, (75 MHz)•: 29.30, 59.01, 70.44, 96.27, 131.10, 133.73, 182.18; HRMS (FAB): [M]$^+$ Calcd for C$_{14}$H$_{22}$O$_5$S, 302.9. Found 303.

Example-3

Preparation of the Assay Having Formula 1

A suspension of sodium hydride (12 mmol) in dry THF was added slowly to a solution of the bisphosphonate (example 1b) (2 mmol) and glycolated thiophene carbaldehyde example 2a (4 mmol) in THF. After refluxing for 12 h, the reaction mixture obtained was cooled followed by the removal of the THF under reduced pressure to give a pasty residue. The residue was suspended in water and extracted with dichloromethane. The organic layer was washed with brine, dried over Na$_2$SO$_4$ and concentrated to give the crude product, which was further purified by column chromatography over silica gel using petroleum ether as eluent. Yield 40-45%; yellow pasty solid (formula 1); $^1$H NMR (300 MHz, CDCl$_3$, TMS)•(ppm): 8.7 (s, 1H, aromatic), 8.3 (m, 1H, aromatic), 7.8 (m, 1H, aromatic), 7.39 (1H, vinylic), 7.15 (1H, vinylic), 7.0 (s, 1H aromatic), 6.8 (s, 1H, aromatic), 3.6 (m, 12H), 3.5 (m, 2H), 3.3 (s, 3H, —OCH$_3$); $^{13}$C NMR CDCl$_3$, (75 MHz)•: 30.70, 58.90, 70.20, 71.80, 120.83, 122.19, 128.56, 132.80, 137.12, 141.93, 147.87, 154.39; HRMS (FAB): [M]$^+$ Calcd for C$_{40}$H$_{52}$N$_2$O$_8$S$_2$, 752.32. Found 753.0.

Example-4

Preparation of the Assay Having Formula 2

The assay having formula 2 can be prepared in solution by monitoring the absorption changes of assay with formula 1 (6×10$^{-6}$M) with the addition of ZnCl$_2$ (4×10$^{-4}$M) in 3 mL acetonitrile water HEPES buffer at pH 7.2. The shift in the absorption maximum at 379 nm to 408 nm indicates the formation of the complex with formula 2. The binding event is also followed by a color change from color less to pale yellow which is the characteristics of cyanide assay with formula 2.

Example-5

(a) Preparation of 9-(2,5,8,11-tetraoxamidecan-13-yl)-9H-carbazole-3-carbaldehyde (glycolated carbazole carbaldehyde)

To a two-neck RB flask under argon atmosphere, POCl$_3$ (0.320 mL, 3.65 mmole) were taken and allowed to stir in an ice cold condition. Dimethyl formamide (DMF), (1.1 mL, 14.6 mmol) were added slowly into it. The reaction mixture was allowed to stir for 1 h. After the formation of the ylide (pale yellow color), glycolated carbazole (1 gm, 3.65 mmol) was added slowly into the reaction mixture. After 12 h, the reaction mixture was poured into ice water in a beaker. A fresh solution of 0.5 N NaOH was added and heated up to 80° C. The solution was then extracted with dichloromethane and purified using silica gel column chromatography (100-200 mesh, 30% ethylacetate-hexane as eluent). A pale yellow liquid was obtained. Yield 60%. $^1$H NMR (300 MHz, CDCl$_3$, TMS)•(ppm): 10.09 (s, —CHO), 8.61 (s, 1H, aromatic), 8.15 (d, 1H, aromatic), 8.02 (d, 1H, aromatic), 7.50 (m, 3H, aromatic), 7.32 (m, 1H, aromatic), 4.5 (t, 2H), 3.9 (t, 2H), 3.56 (m, —OCH$_2$), 3.49 (m, —OCH$_2$), 3.34 (s, —OCH$_3$); FAB-MS: [M]$^+$ Calcd for C$_{22}$H$_{27}$NO$_5$, 385.19. Found 385.6.

Example-6

Preparation of the Assay Having Formula 3

A suspension of sodium hydride (12 mmol) in dry THF was added slowly to a solution of the bisphosphonate (example 1b) (2 mmol) and glycolated carbazole carbaldehyde example 5a (4 mmol) in THF. After refluxing for 12 h, the reaction mixture obtained was cooled followed by the removal of the THF under reduced pressure to give a yellow solid residue. The residue was suspended in water and extracted with dichloromethane. The organic layer was washed with brine, dried over Na$_2$SO$_4$ and concentrated to give the crude product, which was further purified by column chromatography over basic alumina using petroleum ether as eluent. Yield 50%; yellow crystalline solid (formula 3); $^1$H NMR (300 MHz, CDCl$_3$, TMS)•(ppm): 8.81 (d, 2H, aromatic), 8.43 (d, 2H, aromatic), 8.26 (s, 2H, aromatic), 8.14 (d, 2H, aromatic), 8.03 (dd, 2H, aromatic), 7.72 (dd, 2H, aromatic), 7.47 (m, 8H, aromatic), 7.28 (2H, vinylic), 7.20 (2H, vinylic), 4.52 (t, 4H —NCH$_2$), 3.89 (t, 4H, —OCH$_2$), 3.5 (m, 12H), 3.4 (m, 4H), 3.3 (s, 6H, —OCH$_3$); $^{13}$C NMR CDCl$_3$, (75 MHz)•: 43.34, 59.00, 70.55, 71.01, 71.85, 109.17, 118.95, 120.83, 122.19, 126.01, 128.19, 131.83, 132.98, 133.51, 140.80, 141.05, 147.94, 154.24; FAB-MS: [M]$^+$ Calcd for C$_{56}$H$_{62}$N$_4$O$_8$, 831.01. Found 832.66.

Example-7

Preparation of the Assay Having Formula 4

The assay having formula 4 can be prepared by mixing formula 3 with ZnCl$_2$ in 1:1 ratio with a little chloroform at room temperature. The solid powder of the assay was obtained by evaporating the solvent under reduced pressure. The color of the assay was found to be orange. The powder was highly fluorescent under UV light (365 nm). The powder of assay has been used for the fabrication of device.

Example-8

Photograph Showing Binding Event and Fluorescent Changes

The cyanide assay having formula 2 (6×10$^{-6}$M) was dissolved in 4:1 acetonitrile/water buffered at pH 7.2, HEPES). Tetrabutyl ammonium salts of various anions like I$^-$, Cl$^-$, Br$^-$, F$^-$, N$_3^-$, HSO$_4^-$, HClO$_4^-$, OAc$^-$ (1×10$^{-4}$) (20 times excess) and CN—(4×10$^{-4}$M) were added. The vials were illuminated with 365 nm UV light. All other anions shows no fluorescence change except for cyanide anion. A green to blue fluorescence change was observed in the case of CN— anions. Picture of the illuminated vials were photographed using a digital camera.

Example-9

Fluorescence intensity monitoring with biotek cell reader: Cyanide assay having formula 2 (6 μM) in acetonitrile/water 4:1 HEPES at pH 7.2 were taken in a 96 well plate. 22 wells were occupied by 200 μL solution of 2. To the first 10 wells, tetrabutylammonium slats of various anions such as CN—, I—, Cl—, Br—, F—, N3-, ClO4-, HSO4-, OAc—, NO3- (10 μL each) per well added and the emission intensity were recorded. In the next 12 cells 20 equivalents excess of all anions with one equivalent cyanide anions were added and then the emission intensity were recorded. Thus obtained data of fluorescence intensity variation were plotted against different anions as shown in FIG. 5. A clear selectivity can be observed for assay having formula 2 with CN— anions.

Example-10

The assay based on complex of thiophene end-capped bipyridine (formula 1) with zinc ions (formula 2) can be used quantitatively in solution state for selective detection of cyanide anions in biorelevant and analytical samples. This was established by analyzing the total cyanide anion content in various plant varieties. Cassava (*manihot esculenta*) is known to bear cyanogenic glycosides in plant parts such as leaves, shoots and roots. Analysing the total cyanogenic content in the roots of cassava, which is a main food source of tropical regions, is important. Using assay having formula 2 the amount of these glycosides were determined and estimated with the help of standard addition method. Experiment with plant latex: Latex of 3 different plants were selected for analysis 1. Cassava, 2. Mango, and 3. Papaya. Fresh latex from 3 month old cassava plants were collected (300 μL) and diluted with ice cold water to 1 mL. Samples were centrifuged at 1000 rpm for 10 minutes to remove solid residues. The supernatant solution were used as such for analysis. Similarly 300 μL of latex were collected from mango and papaya fruits for a comparative analysis. Increasing volume of plant latex samples were added to assay having formula 2 in a 96 well plate, and recorded the fluorescence intensity variation at 480 and 530 nm. A graph is plotted with variation of intensity with that of plant varieties (FIG. 6). Cassava plant latex only shows variation in the fluorescence intensity which indicates the presence of CN— anions in the samples.

Example-11

The reusability of assay with formula 2. When cyanide anions react with the assay having formula 2, the compound having formula 1 will be regenerated. This allows reusing the probe again for whole process. The regenerated compound can again be complexed with one equivalents of formula 1 $ZnCl_2$ solution to get assay of formula 2. To 3 mL 6 μM solution of formula 2 in acetonitrile-water mixture 40 μL $4\times10^{-4}$M tetrabutyl ammonium cyanide solution in aqueous solution were added. The zinc ion complexed with assay with formula 1 were decomplexed resulted in the generation of blue fluorescence at 480 nm. The cycle can be repeated several times by the addition of zinc ions as well as CN— anions. FIG. 7

Example-12

Thermoplastic support was cut as shown in FIG. 8, as 10 cm long and having 4 mm radius. Assay powder (formula 4) containing alumina is carefully fixed over the surface of the support which is called as dipstick. A 25 mL beaker containing tetrabutyl ammonium cyanide ($2\times10^{-4}$ M) is taken and the stick is dipped in it, followed by the agitation of the stick in the solution. Whenever the analyte is in contact with the stick a color was change from orange to yellow. This is followed by a fluorescence change. The fluorescence change was from orange to a yellowish green. The dipstick removed from the test sample is rinsed in aqueous $ZnCl_2$ solution. After that the stick is washed with pure water and now the sick is ready for another application.

Details of Cell Culturing and Imaging:
Preparation of the Culture Medium

The culture medium was prepared by dissolving 8.4 g of RPMI-1640 (Sigma, USA) in one litre of distilled water. Sodium bicarbonate (2 g/L) was added to the medium and pH of the medium was adjusted to 7.3. This medium was then sterilized by passing through sterile filter assembly fitted with 0.22 μm filter (Millipore, USA) using vacuum pump. Later, the medium was stored in pre-sterilized Borosil polypropylene bottles, at 4° C., for further use.

Preparation of Complete Medium

To the prepared culture medium an antibiotic mixture (20 μL/mL of 100× concentrate, Sigma, USA) was added. Fetal calf serum (FCS) (Sigma, USA) was also added to the medium to give a final concentration of 10% (to 900 mL medium, 100 mL of FCS was added).

Cell Revival

Breast cancer cell lines (MCF-7), were stored in cryovials at −180° C. in liquid nitrogen, in a medium containing 70% FCS, 10% Dimethyl sulfoxide (DMSO) and 20% RPMI-1640 media. For revival, the vials were thawed by placing them in a water-bath maintained at 37° C. Cells were then transferred into a radiation sterilized culturing flask, T-25 cm² (Corning, USA) inside the laminar flow. Subsequently, the flask was placed in $CO_2$ incubator for 2 h. The viable cells, stick to the culture flask while the dead cells remain in the medium. Later the medium was replaced with fresh medium containing 10% FCS and incubated till a monolayer was formed.

Subculturing of MCF-7 Cells

A 25 cm² cell culture flask, which had a uniform monolayer of MCF-7 cells, was taken and its medium was then discarded. Since the MCF-7 cells are adherent in nature, they were trypsinised by using 5 mL of trypsin (0.25%)-EDTA (0.53 mM) buffer containing 0.9% sodium chloride for 5 min. The cells were then transferred to a centrifuge tube and centrifuged at 2000 rpm for 10 min., followed by the removal of the supernatant. For sub culturing, fresh RPMI-1640 media containing 10% FCS was added under aseptic conditions. Cells were flushed with the help of pipette tip (1 mL) till all the cells come into the medium. The cells were then diluted in a sterile complete medium at 1:3 times and transferred into fresh culture flasks. Then the flasks were placed inside $CO_2$ incubator.

Cell Imaging

For imaging, the cells were taken after trypsinisation and addition of fresh media. Approximately, $1\times10^6$ cells/mL was incubated with 1 (6 μM) for 30 min. For the removal of background fluorescence in the medium, the cells were centrifuged at 2000 rpm for 10 minutes and were resuspended in fresh medium. These cells were then imaged using fluorescence microscope at an excitation source of 440 nm.

The main advantages of the present invention are;
1) The excellent selectivity shown by the assay with formula 1 towards $Zn^{2+}$ ions among other biologically important metal ions such as $Na^+$, $K^+$, $Mg^{2+}$, $Ca^{2+}$, $Cu^{2+}$, $Fe^{2+}$, $Hg^{2+}$ etc. The binding event can be distinguished by color change from color less to pale yellow along with intense changes in the fluorescence of the assay from blue to green. This provides rather valuable and distinguishable information about to easily discriminate zinc ions from other metal ions.

2) The assay with formula 1 can be used to image $Zn^{2+}$ in MCF7 cell lines. The selective fluorescence change for $Zn^{2+}$ ions inside cell can be monitored with the help of fluorescence microscopy.

3) The excellent selectivity shown by the assay with formula 2 towards cyanide anions (CN—) among other biologically important anions such as $F^-$, $Cl^-$, $Br^-$, $I^-$, $HClO_4^-$, $HSO_4^-$, $N_3^-$, $NO_3^-$ etc. The binding event with cyanide anion is a based on an analyte replacement protocol that can be distinguished by color change from pale yellow to color less along with intense changes in the fluorescence of the assay green to blue. This provides rather valuable and distinguishable information about to easily discriminate cyanide from other anions.

4) The zinc complex of thiophene end-capped bipyridine assay having formula 2 in acetonitrile/water 4:1 solution can be used to quantify the amount of cyanide anions with a maximum detection limit of 0.104 ppm in solutions, using spectroscopic techniques (UV-spectrophotometer and fluorimeter). In addition to this, the assay having formula 1 can be more conveniently used for detecting zinc ions from aqueous samples.

5) The reversibility of the present assay (Formula 2 and formula 4) (ie; the reusability) is another promising aspect of this invention for its practical application. The probe which is once used for the detection of cyanide anion can be used again by complexing with zinc ions.

6) The fabrication of the present device is so comfortable that it can be handled and used very easily and needs no expertise or sophisticated machineries.

We claim:

1. A zinc complex of an end-capped bipyridine of general formula B

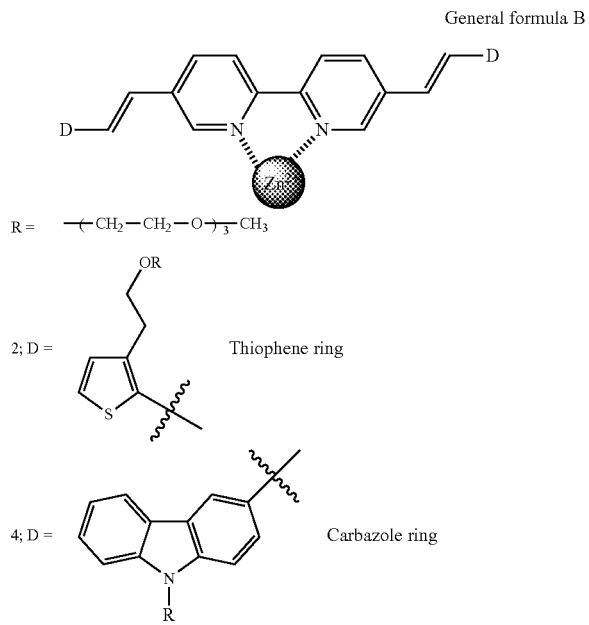

General formula B wherein the said compound is denoted by formula 2 where D is a thiophene ring, and by formula 4 where D is a carbazole ring.

2. A process for the preparation of zinc complex of end-capped bipyridine compound of formula B as claimed in claim 1 comprising the steps of:
   (i) reacting 5,5'-dimethyl-2,2'-bipyridine and N-bromosuccinimide in dry carbon tetrachloride in presence of AIBN as catalyst in the ratio of 10 mmol:20.5 mmol, in carbon tetrachloride at temperature ranging between 80-85° C., for a period ranging between 18-20 h,
   (ii) cooling the reaction mixture and filtering to obtain the filterate, removing the solvent under reduced pressure to obtain the compound 5,5'-bis(bromomethyl)-2,2'-bipyridine (bisbromomethyl),
   (iii) reacting 5,5'-bis(bromomethyl)-2,2'-bipyridine (bisbromomethyl) obtained in step (ii) with triethylphosphite as reactant cum solvent in the ratio of 2 mmol:3 ml, at a temperature ranging between 80-100° C., for about 10-12 h, at normal pressure, and purifying by partial vacuum to obtain 5,5'-Bis-(diethyl phosphonomethyl)-2,2'-bipyridine (Bisphosphonate),
   (iv) reacting 5,5'-Bis-(diethyl phosphonomethyl)-2,2'-bipyridine (Bisphosphonate) (2 mmol) with 3-(2,5,8,11-tetraoxamidecan-13-yl)thiophene-2-carbaldehyde (glycolated thiophene carbaldehyde) or glycolated carbazole carbaldehyde (4 mmol) in presence of sodium hydride (12 mmol) in 30 ml THF, at a refluxing temperature 65-70° C., for a period ranging between 10-15 h, to obtain a thiophene end capped bipyridine compound or a carbazole end capped bipyridine compound (compound 1 and 3 respectively),
   (v) reacting the compounds 1 and 3 obtained in step (iv) above with $ZnCl_2$ to obtain the zinc complex of formula B (compound 2 and 4 respectively).

3. The process as claimed in claim 2, wherein the glycolated thiophene carbaldehyde or glycolated carbazole carbaldehyde is prepared by reacting 3-(2,5,8,11-tetraoxamidecan-13-yl)thiophene or glycolated carbazole with phosphorous oxychloride in presence of DMF for a period ranging 12 hr at 27° C.

4. A method of processing for quantitative analysis of cyanide anions ($CN^-$) using the compound of formula 2 as claimed in claim 1 comprising the steps of:
   (i) adding assay of formula 2 in acetonitrile/water mixture having acetonitrile and water in the ratio of 4:1 to the biological or clinical or industrial samples;
   (ii) determining the concentration of cyanide anions using UV absorption spectrometry and spectrofluorimetry.

5. A dipstick device useful for selective detection of cyanide ions ($CN^-$) in solution, comprising:
   (i) zinc complex of carbazole end capped bipyridine assay powder of formula 4 having bright orange fluorescence, adsorbed over alumina

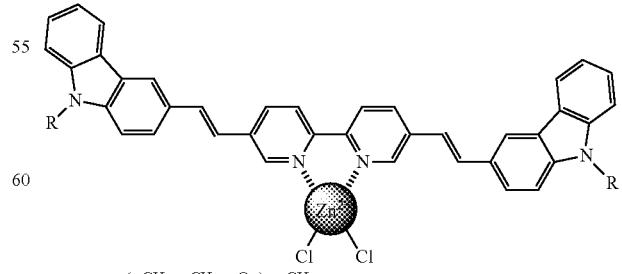

the said material of step (i) being deposited or fixed over the surface of a thermoplastic strip support.

6. The dipstick device as claimed in claim 5, wherein the said device is capable of analysing a sample containing cyanide ions concentrations up to a lower limit of $2 \times 10^{-4}$M.

7. A method for selective detection of cyanide ions (CN$^-$) in solution, using a dipstick device of claim 5, wherein the step of detection comprises contacting the dipstick with a test sample, followed by monitoring a change in fluorescence colour, wherein a change in orange fluorescence colour to yellowish green colour indicates the presence of cyanide ions in the test sample.

* * * * *